United States Patent [19]

Engelhard et al.

[11] 4,024,077

[45] May 17, 1977

[54] CATALYSTS FOR THE ISOMERIZATION OF HYDROCARBONS, AND PROCESS FOR THE PREPARATION OF SAID CATALYSTS

[75] Inventors: Philippe Engelhard; Michel Legendre, both of Le Havre, France

[73] Assignee: Compagnie Francaise de Raffinage, France

[22] Filed: July 31, 1975

[21] Appl. No.: 600,604

[30] Foreign Application Priority Data

Aug. 7, 1974 France .............................. 74.27478

[52] U.S. Cl. .............................. 252/442; 252/432; 252/441; 252/455 R; 252/462; 252/466 PT
[51] Int. Cl.² .................... B01J 23/10; B01J 23/40; B01J 27/08; B01J 27/10
[58] Field of Search .......... 252/432, 441, 442, 462, 252/466 PT, 455 R; 260/683.75

[56] References Cited

UNITED STATES PATENTS

| | | | |
|---|---|---|---|
| 2,814,599 | 11/1957 | LeFrancois et al. | 252/441 X |
| 2,900,425 | 8/1959 | Bloch et al. | 252/442 X |
| 2,998,467 | 8/1961 | Gilbert | 252/442 X |

*Primary Examiner*—W. J. Shine
*Attorney, Agent, or Firm*—Curtis, Morris & Safford

[57] ABSTRACT

Isomerization catalysts for hydrocarbons, and particularly for normal paraffins and/or naphthenes, formed of the following:
  at least one platinum-group metal, preferably platinum;
  at least one element selected from the group consisting of rare earth metals and yttrium; and
  at least one metal halide, for example aluminum trichloride,
  a carrier for the foregoing metals and halide which is formed in whole or in part of at least one refractory mineral oxide, such as alumina, and additionally a halogen in combined form, preferably chlorine. Also a process for the preparation of the foregoing catalysts involving at least one impregnation of the carrier with at least one solution containing at least one of the elements yttrium, rare earth metals, and platinum-group metals; at least one of the impregnating solutions including ions of the foregoing elements except the platinum-group metals; and an aftertreatment by known means with at least metal halide, preferably selected from the group consisting of aluminum trichloride, aluminum tribromide, ferric chloride, ferric bromide, beryllium dichloride, and zinc dichloride. Further modifications of said process including acidification with hydrochloric acid, calcination of the deposited metals, adjustment of the halogen content, and elimination of excess metal halide not fixed on the catalyst. Finally the use of the foregoing catalysts in the isomerization of hydrocarbons.

25 Claims, No Drawings

CATALYSTS FOR THE ISOMERIZATION OF HYDROCARBONS, AND PROCESS FOR THE PREPARATION OF SAID CATALYSTS

The present invention relates to new catalysts for the isomerization of hydrocarbons, and particularly of normal paraffins and/or naphthenes. It further relates to the application of said catalysts to the isomerization of hydrocarbons.

Many isomerization catalysts of widely varying compositions have been proposed in the past. As a rule, the catalyst consists of one or more metals supported on a carrier such as alumina, an aluminosilicate or a mixture of the two. Among the metals making up the known catalysts are the noble metals, and particularly platinum, in association with tin, nickel, germanium, rhenium, lead or the metals of groups Ib, IIb, Vb, VIIb, III or IV of the periodic table of the elements. A metal halide of Friedel and Crafts, such as aluminum trichloride, is further a part of the catalytic formulation comprising the metals and the carrier.

The catalysts may be prepared by methods which differ somewhat from one another. For example, French Pat. No. 1,327,008 describes a method of preparation of a platinum-alumina-aluminum trichloride catalyst in which the platinum is first deposited on the alumina, quite conventionally, by impregnation. The solid obtained is calcined, then reduced with hydrogen. This is followed by a treatment under hydrogen pressure, and heat, with anhydrous aluminum trichloride. The catalyst is then brought to a temperature in the neighborhood of 400° C in a nitrogen atmosphere.

French Pat. No. 2,175,524 describes the preparation of platinum-rhenium or germanium-aluminum trichloride catalysts on alumina. First the metals are deposited on the carrier by impregnation. Then the chlorine content is adjusted while hot, with a mixture of steam and hydrogen chloride, followed by a calcination and a reduction with hydrogen (in the case of platinum-germanium) or directly by drying, calcination and reduction (in the case of platinum-rhenium). These operations are followed by a treatment with aluminum trichloride under hydrogen pressure, as previously described in U.S. Pat. No. 1,327,008, mentioned earlier.

An object of the present invention is to provide new catalysts for the isomerization of hydrocarbons.

The applicants have developed catalysts possessing very good activity and very good selectivity, as will be described further on.

The invention consequently has as a first preferred embodiment catalysts for the isomerization of hydrocarbons comprising at least one platinum-group metal, preferably platinum;

at least one element from the group of rare earth metals and yttrium; and at least one metal halide, in association with a carrier consisting, in whole or in part, of at least one refractory mineral oxide, said catalyst comprising, moreover, a halogen in combined form.

A second preferred embodiment of the invention is a catalyst for the isomerization of hydrocarbons comprising at least one platinum-group metal, preferably platinum;

at least one metal from the group consisting of lanthanum, cerium, yttrium, neodymium, praseodymium, dysprosium, samarium and gadolinium; and at least one metal halide, in association with a carrier consisting, in whole or in part, of at least one refractory mineral oxide, said catalyst comprising, moreover, a halogen in combined form.

A third preferred embodiment of the invention is a process for preparation of an isomerization catalyst in accordance with the invention, said process involving the following steps:

At least one impregnation of the carrier with at least one solution containing at least one of the elements yttrium, lanthanum, cerium, praseodymium, neodymium, dysprosium, samarium, gadolinium and platinum-group metals, at least one of the impregnating solutions comprising either cations formed from the elements yttrium, lanthanum, cerium, praseodymium, neodymium, dysprosium, samarium and gadolinium or anions containing these elements, and an aftertreatment, by means known in the field, with at least one metal halide selected from the group consisting of aluminum trichloride, aluminum tribromide, ferric chloride, ferric bromide, beryllium dichloride and zinc dichloride.

A fourth preferred embodiment of the invention is a process for the isomerization of hydrocarbons, said process consisting in contacting said hydrocarbons, hydrogen and at least one of the catalysts defined above under isomerization conditions known in the field.

As used in this application "platinum-group metal" means a metal from the group consisting of platinum, iridium, osmium, ruthenium, rhodium and palladium.

The catalysts in accordance with the invention comprise at least the refractory oxide carrier. Said carrier may be formed, for example, of alumina, an aluminosilicate, silica, magnesia, zirconia, the oxides of gallium, titanium, thorium or boron, or a mixture of these oxides. However, the applicants have obtained very good results using an alumina with a specific surface between 15 and 350 m$^2$/g, and preferably between 100 and 350 m$^2$/g, and a specific pore volume greater than 0.1 cc/g.

The metals are deposited on the carrier by known means, for example, by impregnation with solutions containing said metals either in anionic form or in cationic form. They may be deposited in any order. The rare earth metals and the platinum-group metal may be deposited simultaneously or successively. However, the applicants have found that it is preferable to deposit the platinum-group metal or metals last, with the last impregnating solution, which does not, however, preclude possible coimpregnation of the carrier with the different metals. The elements from the group consisting of yttrium, lanthanum, cerium, praseodymium, neodymium, dysprosium, samarium and gadolinium may be deposited together or separately. When they are deposited together, the impregnating solution may contain these elements in the proportions of natural mixtures (oxides, for example) of rare earths.

The acidity of the carrier may be altered during the various impregnations, particularly by treatment with an acid solution, for example, a hydrochloric acid solution, before the deposition of at least one platinum-group metal. This has the effect of enhancing the action of the acid sites present on the carrier. The acidic or weakly acidic character, either in the sense of Bronsted or in the sense of Lewis, may be measured. (Hughes, White and White, Journal of Catalysis, 1969, vol. 13, pages 58–64; Tanaka and Ogasaware, Journal of Catalysis, 1970, vol. 16, pages 157–163).

After each deposition of a metal other than a platinum-group metal, the solid obtained may be dried and then possibly calcined at a temperature comprised between 400° and 700° C, and preferably between 500° and 650° C. Following deposition of a platinum-group metal, the solid may be calcined at a temperature of preferably less than 550° C.

After deposition of the various metals selected from the groups mentioned above, the solid obtained contains:

From 0.02 to 2.2 wt.%, and preferably from 0.10 to 0.75 wt.%, of at least one platinum-group metal. This is the content that is usually employed with catalysts for the conversion of hydrocarbons. To obtain satisfactory catalytic properties, the content of this type of metal is preferably above 0.10%, but for reasons of cost of the solid ultimately obtained it is perferably to not exceed 0.75%, although higher contents up to 2.2% will be appropriate.

From 0.005 to 5.7 wt.%, and preferably from 0.01 to 3.2 wt.%, of at least one of the metals from the group mentioned above. Under 0.005%, the improvement secured over a catalyst containing no platinum is negligible; on the other hand, exceeding 5.7% is pointless. The applicants have found, moreover, that the most efficacious contents are between 0.01 and 3.2%.

From 0.1 to 5.7 wt.%, and preferably from 0.4 to 1.7 wt.%, of a halogen, preferably chlorine. Said halogen is combined with the elements forming the carrier and/or with the elements deposited on the carrier at the end of the impregnating treatment. In the remainder of this specification it will be referred to as the "combined halogen."

The contents set forth above are based on the carrier.

The deposition of all of these elements on the carrier must be followed by a treatment with a metal halide from the group consisting of aluminum trichloride, aluminum tribromide, ferric chloride or bromide, and beryllium or zinc dichloride, or any mixture of these halides. The applicants prefer to use aluminum trichloride.

This treatment may be effected by any appropriate means known in the field. For example, the aluminum trichloride may be sublimed on the product at a temperature comprised approximately between 190° and 700° C, and preferably between 200° and 600° C, under atmospheric or higher pressure, in the presence of diluent gases such as hydrogen, inert gases, or light paraffinic hydrocarbons. The impregnation may be effeted discontinuously, but it is preferable to proceed by passing sublimed alumnum trichloride vapors in admixture with a gas such as hydrogen over the catalyst. The halide attaches itself to the solid previously obtained. However, to eliminate unreacted halide, the catalyst must be brought to a temperature above 300° C and scavenged with an inert gas such an nitrogen. The duration and temperature of this latter treatment depends, of course, on the excess of metal halide remaining unfixed on the catalyst. As a rule, a temperature ranging from 400° to 700° C, and preferably from 500° to 600° C, and a duration of from 1 to 48 hours will suffice to eliminate this excess. The catalyst ultimately obtained at this last step contains from 0.5 to 15%, and preferably from 1 to 10%, of total halogen, based on the total weight of the catalyst, the preferred halogn being chlorine. "Total halogen" means both the "combined halogen", as defined earlier, and the halogen resulting from the treatment with the metal halide.

Before the metal-halide treatment, it is preferable to adjust the "combined halogen" content of the solid to be treated. This adjustment of the "combined halogen" content may be effected, for example, by treatment of said solid with a gaseous mixture of steam and halogen compound, which may be diluted in another gas or mixture of gas such as air, at a temperature between 400° and 700° C — for example, on the order of 500° C. If the halogen is chlorine, a mixture of steam and hydrogen chloride or another chlorinated compound may be used, for example. After this gas treatment, the solid may be dried at a temperature ranging approximately from 95° to 315° C and then calcined at a temperature comprised approximately between 370° and 600° C for a variable time under 10 hours and preferably between 1 and 5 hours.

It is then necessary to treat the solid with an anhydrous gas, that is to say, a gas containing less than 20 ppm of water by volume, just before depositing the metal halide. Good results are obtained by passing a hydrogen stream substantially free from water over the solid at a temperature comprised between 400° and 700° C, and preferably between 400° and 600° C, for a time of about 1 to 10 hours.

The solid so obtained prior to the metal-halide treatment contains slightly more "combined" halogen than the solid obtained after deposition of the metals on the carrier. For example, for solids containing initially from 0.4 to 1.6% of the weight of the composition of "combined" halogen, the solid obtained after the step of adjustment of the halogen content may contain about 0.8 to 2% of "combined" halogen.

The catalysts in accordance with the invention are intended for use in a process for isomerization of hydrocarbons, and more particularly of paraffinic and/or naphthenic hydrocarbons. The conditions of isomerization temperature and pressure are known in the field. Thus, the temperature is comprised between 20° and 450° C, the pressure (hydrogen pressure) between 1 atm and 100 atm, the molar ratio of hydrogen to hydrocarbons introduced into the reactor ranging from 0.5 to 20, and the space velocity per hour, measured in the liquid state, and estimated in volume of charge passing over a unit volume of catalyst in one hour (LHsv), being comprised between 0.1 and 10. The hydrocarbon charges which may be treated cover a wide range. However, the applicants have found that the catalysts in accordance with the invention are very well suited for the isomerization of paraffinic and/or naphthenic hydrocarbons, apart from xylenes, olefins and other charges.

The catalysts ultimately obtained have been found to be more advantageous than a catalyst containing only platinum and a metal halide deposited on a refractory mineral oxide carrier, as shown by the following examples, which are in no wise limitative and are given merely by way of illustration.

In this example, the charge used is simply normal pentane, which, however, should not be construed as a limitation. This particular hydrocarbon is generally used to test catalysts for their aptitude for isomerization, just as normal heptane is the hydrocarbon used to test the capacities of reforming catalysts.

EXAMPLE I

This example relates to the preparation and utilization of a dozen catalysts in accordance with the invention. It describes successively the preparation of the twelve catalysts A1, A2, B1, B2, C1, C2, D, E, F, G, H and I as well as of their control catalysts T1, T2, and T3, and then their application to the hydroisomerization of normal pentane.

PREPARATION OF CATALYSTS

The refractory carrier used with all the catalysts below is an alumina whose characteristics are as follows:

| | |
|---|---|
| Specific surface | 190 m²/g |
| Pore volume | 0.51 cc/g |
| Average pore radius | 53 Å |
| Chlorine content (measured by x-ray fluorescence) | 0.4% by weight of the alumina |
| Form | Extrudates with an average diameter of 1.5 mm |

This alumina is calcined for 4 hours at 600° C before the various metals are deposited.

CONTROL CATALYSTS T1, T2 AND T3

The above alumina is immersed in an approximately 0.1 N dilute hydrochloric acid solution. After dewatering at ambient temperature, the alumina is contacted with a circulating solution of hexachloroplatinic acid whose initial platinum concentration is such that the catalyst contains about 0.35% by weight of platinum. After dewatering followed by drying at 100° C, the solid is calcined at about 530° C in a muffle kiln. The catalyst so obtained contains about 0.31% of platinum.

The solid is then subjected to a treatment for adjustment of its chlorine content. To this end, a gaseous stream of steam and hydrogen chloride is passed over it at 500° C for 4 hours. The solid obtained is then calcined for 1 hour at the same temperature.

Finally, the solid is subjected to a reduction with hydrogen for about 1 hour at 500° C. It contains 1.15% of chlorine, apart from 0.31% of platinum.

In order to obtain three control catalysts which differ only as a result of the subsequent aluminum trichloride treatment, the solid obtained after reduction is divided into three portions which are then subjected independently to said treatment.

13 grams of the solid obtained is scavenged with a stream of sublimed aluminum trichloride and hydrogen (total pressure of gas stream, 1 atm; partial pressure of aluminum trichloride, 30 mmHg) for 2 hours at 300° C, then for ½ hour at 420° C.

Finally, the three control catalysts T1, T2 and T3 obtained are treated with an anhydrous nitrogen stream at about 500° C so as to eliminate the unreacted aluminum trichloride.

Thus the three controls T1, T2 and T3 are obtained whose characteristics are presented in Table 1.

CATALYSTS A1 AND A2

100 g of the above alumina is impregnated with 250 cc of a solution containing 20 cc hydrochloric acid RP and 0.190 g yttrium oxide, $Y_2O_3$. After dewatering the solid is dried at about 120° C, then calcined for 2 hours at 600° C.

This is followed by an acidification of the carrier, and impregnation with a hexachloroplatinic acid solution, an adjustment of the chlorine content, and a reduction with hydrogen identical in every respect with the operations described in connection with the control catalysts T1, T2 and T3.

The solid obtained is then divided into two portions:

The first portion (13 grams) is made to undergo a treatment with an $AlCl_3/H_2$ mixture (identical to that previously employed for T1, T2 and T3) for 2 hours at 250° C, then for ½ hour at 420° C. After scavenging with an anhydrous nitrogen stream at 500° C, the catalyst A1 (see Table I) is obtained.

The second portion (13 grams) is subjected to the same treatment but only at 300° C for 2½ hours. After scavenging with an anhydrous nitrogen stream at 500° C, catalyst A2 (see Table I) is obtained.

CATALYSTS B1 AND B2

100 g of the above alumina is impregnated with 250 cc of a solution containing 20 cc of hydrochloric acid RP and 0.730 g of lanthanum nitrate, $La(NO_3)_3 \cdot 6H_2O$. After dewatering, the solid is dried at about 120° C, then calcined for 2 hours at 600° C.

The subsequent treatments are the same as those applied to obtain catalysts A1 and A2. In this way, catalysts B1 and B2 (see Table I) are obtained.

CATALYSTS C1 AND C2

The same procedure is followed, except that here the first impregnating solution contains, not yttrium or lanthanum but 0.732 g of cerium nitrate, $Ce(NO_3)_3 \cdot 6H_2O$.

The subsequent treatments, already described in connection with A1 and A2, result in the catalysts C1 and C2 (see Table I.

CATALYST D

The same procedure is followed, except that in this test the first solution contains 0.287 g of praseodymium oxide, $Pr_6O_{11}$. The solid obtained is dried and calcined as described previously. This is followed by the preparation described for catalyst A2 (deposition of platinum, adjustment of chlorine content, reduction with hydrogen, and then treatment with $AlCl_3$ and $H_2$ at 300° C for 2 hours and scavenging with nitrogen).

CATALYST E

In this case, the first impregnating solution contains 0.283 g of neodymium oxide, $Nd_2O_3$, which is the only difference with respect to preparation of catalyst D.

CATALYST F

The same procedure is followed as with catalyst E, except that the first impregnating solution contains 0.3143 g of dysprosium oxide, $Dy_2O_3$.

CATALYST G

The same procedure is followed as with catalyst F, except that the first impregnated solution contains 0.2964 g of samarium oxide, $Sm_2O_3$.

CATALYST H

The same procedure is followed as with catalyst G, except that the first impregnating solution contains 0.3054 g of gadolinium oxide, $Gd_2O_3$.

CATALYST I

The same procedure is followed as with catalyst H, except that the first impregnating solution contains 0.2432 g of lanthanum nitrate, $La(NO_3)_3 \cdot 6H_2O$; 0.0956 g of praseodymium oxide, $Pr_6O_{11}$; and 0.0945 g of neodymium oxide $Nd_2O_3$.

Table I below shows the characteristics of the products obtained
- after impregnation with the metallic constituents, and
- after calcination of 530° C.

The table also lists the conditions (temperature and duration) of the treatment with the gaseous aluminum tricholoride-hydrogen mixture.

Table I

| Catalyst | Composition, in wt. %, of solid calcined at 530° C | | | Treatment with $AlCl_3 + H_2$ | Final chlorine content |
|---|---|---|---|---|---|
| | Pt | Cl | Other metals | | |
| T1 | 0.31 | 1.15 | 0 | 2 hr at 300° C, ½ hr at 420° C | 5.93 |
| T2 | 0.31 | 1.15 | 0 | " | 5.77 |
| T3 | 0.31 | 1.15 | 0 | " | 5.72 |
| A1 | 0.37 | 1.19 | 0.05 Y | 2 hr at 250° C, ½ hr at 420° C | 5.61 |
| A2 | 0.37 | 1.19 | 0.05 Y | 2½ hr at 300° C | 5.56 |
| B1 | 0.38 | 1.18 | 0.06 La | 2 hr at 250° C, ½ hr at 420° C | 5.57 |
| B2 | 0.38 | 1.18 | 0.06 La | 2½ hr at 300° C | 5.45 |
| C1 | 0.36 | 1.32 | 0.14 Ce | 2 hr at 250° C, ½ hr at 420° C | 5.50 |
| C2 | 0.36 | 1.32 | 0.14 Ce | 2½ hr at 300° C | 5.93 |
| D | 0.37 | 1.35 | 0.06 Pr | 2½ hr at 300° C | 5.09 |
| E | 0.38 | 1.40 | 0.06 Nd | 2½ hr at 300° C | 5.38 |
| F | 0.36 | 1.24 | 0.16 Dy | 2½ hr at 300° C | 6.04 |
| G | 0.37 | 1.33 | 0.11 Sm | 2½ hr at 300° C | 5.56 |
| H | 0.37 | 1.39 | 0.11 Gd | 2½ hr at 300° C | 5.91 |
| I | 0.37 | 1.30 | 0.02 La 0.02 Pr 0.02 Nd | 2½ hr at 300° C | 5.87 |

CATALYTIC TESTS

Catalytic tests are then performed with each of these catalysts in the following manner:

Normal pentane and hydrogen are passed, at atmospheric pressure and three different temperatures (100°, 130° and 150° C) over 3 cc of catalyst placed in a reactor. The space velocity per hour, defined earlier, is 0.5 and the molar ratio of hydrogen to hydrocarbon is 3.2.

The only product of the reaction is isopentane. The activity of the various catalysts may therefore be estimated on the basis of the conversion of the normal pentane. The results are reported in Table II below for each catalyst and each temperature.

From these results, it is apparent that the catalysts in accordance with the invention possess good activity for isomerization. The platinum-yttrium-aluminum trichloride catalysts come close to the control catalysts while the other catalysts exhibit greater activity.

Table II

| Catalyst | Conversion of normal pentane at test temperature | | |
|---|---|---|---|
| | 100° C | 130° C | 150° C |
| T1 | 14 | 26.4 | 40 |
| T2 | 12 | 26.0 | 42.0 |
| T3 | 13.6 | 26.4 | 42.0 |
| A1 | 10.0 | 26.0 | 38.0 |
| A2 | 12.4 | 28.0 | 40.8 |
| B1 | 15.0 | 33.6 | 44.4 |
| B2 | 17.4 | 36.4 | 51.2 |
| C1 | 17.2 | 36.4 | 50.8 |
| C2 | 15.6 | 36.4 | 53.0 |
| D | 24.0 | 45.2 | 51.8 |
| E | 19.6 | 36.0 | 46.0 |
| F | 14.7 | 30.6 | 42.3 |
| G | 20.3 | 34.3 | 43.7 |
| H | 21.1 | 46.5 | 58.6 |
| I | 15.5 | 32.7 | 43.5 |

EXAMPLE II

This example illustrates the utilization of the catalytic compositions in accordance with the invention in the isomerization, under pressure, of normal pentane.

For this purpose, four catalysts have been prepared in the same manner as in Example I (for catalysts containing the same metals). Table III shows the composition of the catalysts which have been tested under pressure.

TABLE III

| Catalyst | Composition, in wt.% of solid calcinated at 530° C | | | Final chlorine content, after treatment with $AlCl_3 + H_2$ at 300° C for 2½ hr. |
|---|---|---|---|---|
| | Pt | Cl | Other metals | |
| T4 (control) | 0.31 | 1.45 | 0 | 5.85 |
| B3 | 0.38 | 1.18 | 0.06 La | 5.70 |
| C3 | 0.36 | 1.35 | 0.13 Ce | 5.70 |
| H2 | 0.37 | 1.39 | 0.11 Gd | 5.79 |

These catalytic formulations were tested under the following conditions:

| | |
|---|---|
| Molar ratio of hydrogen to hydrocarbons: | 3 |
| Charge: | Normal Pentane |
| Space velocity per hour: | 3.0 |
| Pressure: | 30 bars |
| Temperature: | 150° C |

The reactor effluent was analyzed with a view to determining the percentage of isopentane obtained in the hydrocarbon fraction having five carbon atoms. The results are as follows:

| | |
|---|---|
| T4 (control) | 43% of isopentane |
| B3 | 68% of isopentane |

| | |
|---|---|
| C3 | 63% of isopentane |
| H2 | 71% of isopentane |

These pressure tests thus confirm that the catalysts in accordance with the invention are good catalysts for the isomerization of paraffinic and/or naphthenic hydrocarbons.

We claim:

1. A catalyst for the isomerization of hydrocarbons comprising:
   a platinum-group metal;
   an element selected from the group consisting of yttrium, lanthanum, cerium, praseodymium, neodymium, dysprosium, samarium and gadolinium;
   a metal halide selected from at least one of the group consisting of aluminum trichloride, aluminum tribromide, ferric chloride, ferric bromide, and beryllium dichloride; and a carrier for the foregoing which is formed in whole or in part of at least one refractory mineral oxide, and additionally a halogen in combined form.

2. A catalyst as defined in claim 1, wherein said platinum-group metals comprise from 0.02 to 2.2 wt.%, said element comprises from 0.005 to 5.7 wt.%, said combined halogen content comprises from 0.1% to 5.7 wt.%; and said total halogen content comprises from 0.5 to 15 wt.%; said wt.%—s being based on the total weight of the catalyst.

3. A catalyst as defined in claim 2 wherein said ranges are 0.10 to 0.75 wt.%, 0.01 to 3.2 wt.%, 0.4 to 1.7 wt.%, and 1 to 10 wt.%, respectively for said platinum-group metals, said element, said combined halogen and said total halogen content.

4. A catalyst as defined in claim 2, further comprising said refractory mineral oxide being selected from the group consisting of alumina, the aluminosilicates, silica, zirconia, thorium oxide, magnesia, gallium oxide, boron oxide and any mixture of these compounds.

5. A catalyst as defined in claim 2, further comprising said refractory mineral oxide being an alumina having a specific surface between 15 and 350 m$^2$/g and a specific pore volume greater than 0.1 cc/g, and having acid sites.

6. A catalyst as defined in claim 2, wherein said platinum-group metal is only platinum.

7. A catalyst, as defined in claim 6, wherein said metal halide is aluminum trichloride.

8. A catalyst as defined in claim 7, wherein said carrier has a specific surface of between 100 and 350 m$^2$/g.

9. A catalyst as defined in claim 7, further comprising said refractory mineral oxide being an alumina having a specific surface between 15 and 350 m$^2$/g and a specific pore volume greater than 0.1 cc/g, and having acid sites.

10. A catalyst as defined in claim 1, wherein said metal halide is aluminum trichloride.

11. A catalyst as defined in claim 6, wherein said aforementioned element is selected from the group consisting of cerium, praseodymium, neodymium, dysprosium, samarium and gadolinium.

12. A catalyst for the isomerization of hydrocarbons comprising:
   at least one platinum-group metal;
   at least one element selected from the group consisting of yttrium, lanthanum, cerium, praseodymium, neodymium, dysprosium, samarium and gadolinium;
   at least one metal halide selected from the group consisting of aluminum trichloride, aluminum tribromide, ferric chloride, ferri bromide, and beryllium dichloride, and a carrier for the foregoing which is formed in whole or in part of at least one refractory mineral oxide, and additionally a halogen in combined form;
   and prepared by a process comprising the following steps:
   impregnation of the carrier with (a) a solution containing a compound of at least one of the elements selected from the group consisting of yttrium, lanthanum, cerium, praseodymium, neodymium, dysprosium, samarium and gadolinium and (b) a solution of a compound of at least one platinum-group metal, and
   drying and reducing to said catalyst and
   an aftertreatment with at least one of said metal halides.

13. A catalyst as defined in claim 12, wherein said metal halide is aluminum trichloride, said element is gadolinium, said platinum-group metal is platinum, said halogen is chlorine, said refractory mineral oxide is alumina, having a specific surface between 15 and 350 m$^2$/g and a specific pore volume greater than 0.1 cc/g, and having acid sites, and its components range from 0.02 to 2.2 wt.%; 0.005 to 5.7 wt.%, 0.1 to 5.7 wt.%, and 0.5 to 15 wt.%, respectively for said platinum, gadolinium, combined chlorine, and total chlorine, said weight percentages being based on the total weight of the catalyst.

14. A process for preparation of a catalyst for the isomerization of hydrocarbons said catalyst comprising:
   at least one platinum-group metal;
   at least one element selected from the group consisting of yttrium, lanthanum, cerium, praseodymium, neodymium, dysprosium, samarium and gadolinium;
   at least one metal halide selected from the group consisting of aluminum trichloride, aluminum tribromide, ferric chloride, ferric bromide, and beryllium dichloride, and a carrier for the foregoing which is formed in whole or in part of at least one refractory mineral oxide, and additionally a halogen in combined form;
   said process comprising the following steps:
   impregnation of the carrier with (a) a solution containing a compound of at least one of the elements selected from the group consisting of yttrium, lanthanum, praseodymium cerium, prasedoymium, doeodymium, dysprosium, samarium, and gadolinium and (b) a solution of a compound of at least one platinum-group metal and
   drying and reducing to said catalyst and
   an aftertreatment with at least one of said metal halides.

15. A process as defined in claim 14, wherein in the carrier-impregnation step the platinum-group metal compound is in the last impregnating solution.

16. A process as defined in claim 15, wherein before or during impregnation with at least one platinum-group metal compound the carrier is treated with a solution of hydrochloric acid.

17. A process as defined in claim 14, which comprises, after impregnation with at least one platinum-group metal compound, a calcination at a temperature under 550° C.

18. A process as defined in claim 15 which comprises, after impregnation with at least one element other than the platinum-group metal compound, a drying and then a calcination at a temperature comprised between 400° and 700° C and, after impregnation with at least one platinum-group metal compound, a drying and then a calcination at a temperature under 550° C and reducing to said catalyst.

19. A process as defined in claim 18, further comprising, after the impregnation step and before the treatment with at least one metal halide, the following steps:
   a Adjustment of the halogen content to a content between 0.8 and 2% of the weight of the solid obtained after the impregnation step, by scavenging said solid with a gaseous mixture comprising steam and a halogen compound at a temperature comprised between 400° and 700° C,
   b. Drying of the solid so obtained at a temperature approximately between 95° and 315° C, followed by calcination at a temperature approximately between 370° and 600° C, and
   c. Scavenging of the resulting solid with an anhydrous gas stream at a temperature comprised between 400° and 700° C.

20. A process as defined in claim 19, wherein there is used in step (c) a stream of hydrogen which is substantially free from water, and at a temperature between 400° and 600° C.

21. A process as defined in claim 14, further comprising after the treatment with at least one metal halide, a scavenging of the catalyst obtained with an inert gas, at a temperature above 300° C, for elimination of the excess of metal halide not fixed on the catalyst.

22. A process as defined in claim 20, further comprising after the treatment with at least one metal halide, a scavenging of the catalyst obtained with nitrogen at a temperature between 400° and 600° C, for elimination of the excess of metal halide not fixed on the catalyst.

23. A process as defined in claim 16, wherein said metal halide is aluminum trichloride.

24. A process as defined in claim 20, wherein said metal halide is aluminum trichloride.

25. A process as defined in claim 24, further comprising after the treatment with at least one metal halide, a scavenging of the catalyst obtained with an inert gas, at a temperature above 300° C, for elimination of the excess of metal halide not fixed on the catalyst.

* * * * *

UNITED STATES PATENT AND TRADEMARK OFFICE
CERTIFICATE OF CORRECTION

PATENT NO. : 4,024,077

DATED : May 17, 1977

INVENTOR(S) : Engelhard et al.

It is certified that error appears in the above-identified patent and that said Letters Patent are hereby corrected as shown below:

Claim 12, line 5, "ferri" should be --ferric--.

Signed and Sealed this ninth Day of August 1977

[SEAL]

Attest:

RUTH C. MASON
Attesting Officer

C. MARSHALL DANN
Commissioner of Patents and Trademark